(12) United States Patent
Takakura et al.

(10) Patent No.: US 8,093,047 B2
(45) Date of Patent: Jan. 10, 2012

(54) INDUCTION OF MYOCARDIAL CELL FROM MAMMALIAN BONE MARROW CELL OR CORD BLOOD-DERIVED CELL AND FAT TISSUE

(75) Inventors: Nobuyuki Takakura, Ishikawa (JP); Yoshihiro Yamada, Ishikawa (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 454 days.

(21) Appl. No.: 10/584,028

(22) PCT Filed: Dec. 21, 2004

(86) PCT No.: PCT/JP2004/019666
§ 371 (c)(1),
(2), (4) Date: Jun. 22, 2006

(87) PCT Pub. No.: WO2005/063967
PCT Pub. Date: Jul. 14, 2005

(65) Prior Publication Data
US 2007/0212676 A1 Sep. 13, 2007

(30) Foreign Application Priority Data
Dec. 25, 2003 (JP) ................................ 2003-429088

(51) Int. Cl.
*C12N 5/07* (2010.01)
*C12N 5/0775* (2010.01)
(52) U.S. Cl. ......... 435/377; 435/325; 435/372; 435/373
(58) Field of Classification Search .................. 435/325, 435/372, 373, 377
See application file for complete search history.

(56) References Cited

U.S. PATENT DOCUMENTS

| 4,963,489 A * | 10/1990 | Naughton et al. ............. 435/1.1 |
| 6,555,374 B1 | 4/2003 | Gimble et al. |
| 2002/0142457 A1 * | 10/2002 | Umezawa et al. ............ 435/366 |

FOREIGN PATENT DOCUMENTS

| EP | 1254952 A1 | 11/2002 |
| WO | WO-01/48150 A1 | 7/2001 |
| WO | WO-01/48151 A1 | 7/2001 |

OTHER PUBLICATIONS

Lee et al. 2004. Isolation of multipotent mesenchymal stem cells from umbilical cord blood. Blood.103:1669-1675.*
Gilmore et al. 2000. Ex vivo expansion of human umbilical cord blood and peripheral blood CD34+ hematopoietic stem cells. Experimental Hematology 28:1297-1305.*
Bonnet. 2003. Biology of human bone marrow stem cells. Clin Exp Med (2003) 3:140-149.*
Rangappa et al. 2003. Transformation of Adult Mesenchymal Stem Cells Isolated From the Fatty Tissue Into Cardiomyocytes. Ann Thorac Surg 2003;75:775-9.*
Egger et al. 2004. Epigenetics in human disease and prospects for epigenetic therapy. Nature. 429:457-463.*
The Chemistry of Health. Glossary from National Institute of General Medical Science. 2009. http://publications.nigms.nih.gov/chemhealth/glossary.html. p. 1-5.*
Fukuhara et al., The Journal of Thoracic and Cardiovascular Surgery, vol. 125, No. 6, pp. 1470-1480, Jun. 1, 2003 XP-002411394.
Rangappa et al., The Journal of Thoracic and Cardiovascular Surgery, vol. 126, No. 1, pp. 124-132 Jul. 1, 2003 XP-002411395.
Zuk et al., The American Society for Cell Biology, vol. 13, No. 12, pp. 4279-4295, Dec. 20, 2002, XP-002249630.
Yamada, Y. et al., "Cardiac Progenitor Cells in Brown Adipose Tissue Repaired Damaged Myocardium", Biochemical and Biophysical Research Communications, 2006, vol. 342, pp. 662-670.
Yamada, Y, et al., "A Novel Approach for Myocardial Regeneration with Educated Cord Blood Cells Cocultured with Cells from Brown Adipose Tissue", Biochemical and Biophysical Research Communications, 2007, vol. 353, pp. 182-188.
Yamada, Y. et al., "Cardiac Stem Cells in Brown Adipose Tissue Express CD133 and Induce Bone Marrow Nonhematopoietic Cells to Differentiate into Cardiomyocytes", Stem Cells, 2007, vol. 25, pp. 1326-1333.

* cited by examiner

*Primary Examiner* — Taeyoon Kim
(74) *Attorney, Agent, or Firm* — Birch, Stewart, Kolasch & Birch, LLP

(57) ABSTRACT

This invention provides a method for differentiating mammalian bone marrow cells or cord blood-derived cells into myocardial precursor cells and/or myocardial cells by culturing said bone marrow cells or cord blood-derived cells with cells isolated from mammalian fat tissues or a culture supernatant thereof.

10 Claims, 9 Drawing Sheets
(6 of 9 Drawing Sheet(s) Filed in Color)

A.

B.

GATA-4

NKX2.5

G3PDH

US 8,093,047 B2

INDUCTION OF MYOCARDIAL CELL FROM MAMMALIAN BONE MARROW CELL OR CORD BLOOD-DERIVED CELL AND FAT TISSUE

TECHNICAL FIELD

The present invention relates to a technique of inducing mammalian bone marrow cells or cord blood-derived cells and fat tissues to differentiate into myocardial cells.

BACKGROUND ART

Myocardial cells stop their proliferation upon the maturation of a host. Accordingly, restoration of myocardial cells could not be expected in a heart that has been once afflicted with myocardial infarction, and the heart was considered to be a nonregenerative organ. In recent years, however, the existence of myocardial precursor/stem cells was discovered in the heart, and division thereof or differentiation thereof into myocardial cells was occasionally observed (Beltrami A. P., et al., "Adult Cardiac Stem Cells Are Multipotent and Support Myocardial Regeneration," Cell, Vol. 114, pp. 763-776, 2003). The development of a technique for inducing ectopic cells, which can be differentiated into myocardial cells, to differentiate into myocardial cells enables the treatment of myocardial infarction, which was difficult in the past.

Master cells of the fetal period, i.e., embryonic stem cells (ES cells), can be easily differentiated into myocardial cells. However, preparation of ES cells for each patient is ethically problematic, and myocardial cells differentiated from the randomly prepared ES cells cause immunological rejection. Thus, ES cells cannot be applied to actual medical practice at present.

The bone marrow stroma comprises multipotent mesenchymal stem cells, and many reports have been heretofore made concerning tissue regeneration techniques utilizing such mesenchymal stem cells. Examples of such techniques include: the regeneration of skeletal muscles utilizing bone marrow-derived myocytes (Ferrari G. et al., "Muscle regeneration by bone marrow-derived myogenic progenitors," Science 1998, 279 (5356), pp. 1528-30); the improvement in cardiac functions via administration of c-kit-positive bone marrow stem cells to the heart (Orlic D, et al., "Bone marrow cells regenerate infracted myocardium," Nature, Vol. 410, No. 5, 2001, pp. 701-705); and the regeneration of cardiac muscles mediated by bone marrow-derived cells (JP Patent Publication (Kohyo) No. 2002-511094 A, WO 01/048151, and JP Patent Publication (Kohyo) No. 2002-521493 A). It is also reported that the mesenchymal stem cells can be differentiated into myocardial cells by adding a demethylating enzyme to the mesenchymal stem cells to reset them (Makino S. et al., "Cardiomyocytes can be generated from marrow stromal cells in vitro," The Journal of Clinical Investigation 103: pp. 697-705, 1999). The myocardial cells prepared via such method have been subjected to demethylation, and thus, they may cause anomalies in the future. Accordingly, clinical application of such myocardial cells would involve considerable difficulties.

Tissue regeneration utilizing mesenchymal stem cells involves the issue of quantitative limitations of the bone marrow to be used, and more extensive resources have been expected for materials for tissue regeneration. Fat tissues are easily obtainable. Multipotent cells have been isolated from human fat tissues, and differentiation thereof into nerve cells was recently observed (Zuk P. A. et al., "Multilineage Cells from Human Adipose Tissue: Implications for Cell-Based Therapies," Tissue Engineering, Vol. 7, No. 2, 2001, pp. 211-228; Zuk P. A. et al., "Human Adipose Tissue Is a Source of Multipotent Stem Cells," Molecular Biology of the Cell, Vol. 13, pp. 4279-4295, 2002). Also, mouse cell strains derived from sarcoblasts that can be differentiated into myocardial cells have also been isolated (JP Patent Publication (Kokai) No. 2003-325169 A and 2003-259863 A). Use of such cells is not practical because of their particularity and the need for a complicated step of culture in order to induce cell differentiation.

DISCLOSURE OF THE INVENTION

An object of the present invention is to provide a technique for easily inducing mammalian bone marrow cells or cord blood-derived cells and fat tissues to differentiate into myocardial cells in vitro.

The present inventors found that mesenchymal cells in fat tissues could be induced to differentiate into myocardial cells in a common culture solution containing bovine serum. They also found that bone marrow cells or cord blood-derived cells can be induced to differentiate into myocardial cells by culturing such cells with the cells isolated from mammalian fat tissues or a culture supernatant thereof.

The present invention provides a method for differentiating mammalian bone marrow cells or cord blood-derived cells into myocardial precursor cells and/or myocardial cells by culturing said bone marrow cells or cord blood-derived cells into myocardial precursor cells and/or myocardial cells with the cells isolated from mammalian fat tissues or a culture supernatant thereof.

In this method, a culture solution preferably comprises cytokines that accelerate differentiation and proliferation in addition to bovine serum. Examples of such cytokines include: members of the EGF family, such as EGF, TGF-α, HB-EGF, FGF, and HGF; members of the TGF-β family, such as TGF-β; members of the IL family, such as LIF; members of the VEGF family, such as VEGF-A; members of the PDGF family, such as PDGF-AB and PDGF-BB; members of the Ephrin family, such as Ephrin B; and the stem cell factor (SCF).

The duration of cell culture is not particularly limited, and culture is preferably conducted for at least 1 day.

In the present invention, bone marrow cells are preferably bone marrow stroma cells, and particularly preferably mesenchymal stem cells. Alternatively, fractions of hematopoietic stem cells are preferably used. For example, mononuclear cells in the cord blood are preferable as cord blood-derived cells.

The ratio of the bone marrow cells or cord blood-derived cells to be mixed with the cells isolated from fat tissues to be cultured together is not particularly limited, and a ratio of approximately 0.1:1 to 1:10 is preferable. More specifically, the ratio of bone marrow cells to be mixed with the cells isolated from fat tissues is preferably approximately 1:4.

Further, the present invention provides myocardial precursor cells and/or myocardial cells prepared via any of the aforementioned methods. Such myocardial precursor cells and/or myocardial cells can suppress the risk of rejection after transplantation, as long as fatty tissues or bone marrow cells obtained from the mammalian as the target of transplantation are used.

The present invention also provides a method for evaluating the effects of a test substance on myocardial precursor cells and/or myocardial cells by adding the test substance to the myocardial precursor cells and/or myocardial cells. Such method can be applied to a test of the drug sensitivity of myocardial cells or screening for therapeutic agents for heart diseases.

According to the present invention, myocardial cells can be easily obtained from mammalian bone marrow cells or cord blood-derived cells and fat tissues. The resulting myocardial cells are highly safe because they have not been subjected to genetic engineering, and they exhibit gene expression patterns or phenotypic traits peculiar to myocardial cells. Thus, the myocardial precursor cells and/or myocardial cells obtained by the method of the present invention can be applied to the evaluation of drugs for the regeneration of the heart or drugs affecting myocardial cells.

At present, revascularization in the ischemic area, which was generated upon myocardial infarction, is carried out via local transplantation of vascular stem cells obtained from a large amount of bone marrow fluid. Bone marrow fluid is sampled under general anesthesia, which imposes risks on elderly patients. In contrast, fat tissue sampling can be carried out via simple local anesthesia of skin, and a life-threatening risk is rarely imposed on patients. Accordingly, the present invention remarkably contributes to the medical field.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Figure 1:
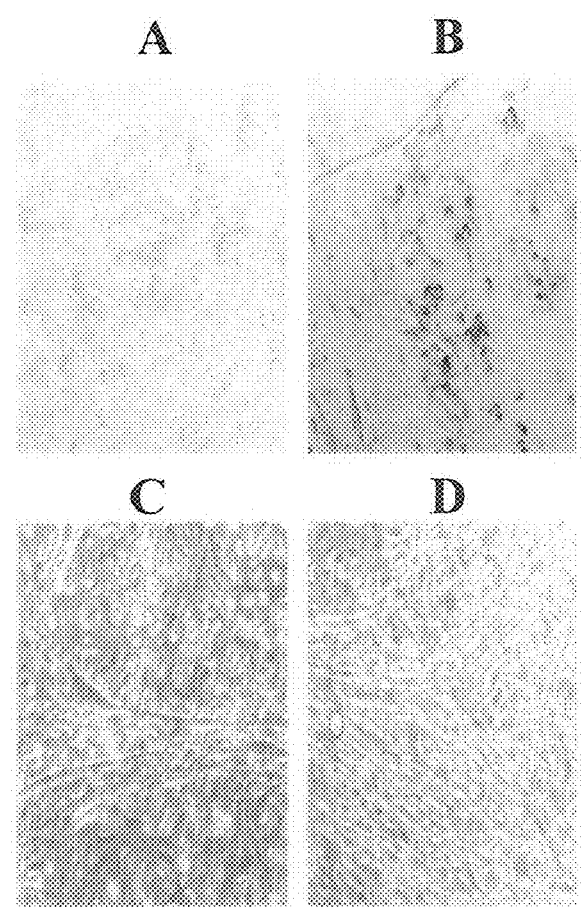
FIG. 1 shows the results of culturing fat tissues (differentiation into myocardial cells) (A: at the time of initiation of culture; B: 7 days after the initiation of culture; C: 14 days after the initiation of culture; D: 28 days after the initiation of culture).

This description includes part or all of the contents as disclosed in the description of Japanese Patent Application No. 2003-429088, which is a priority document of the present application.

PREFERRED EMBODIMENTS OF THE INVENTION

1. A Method of Differentiating Cells Isolated from Fat Tissues into Myocardial Cells Mesenchymal cells in fat tissues can be induced to differentiate into myocardial cells in a common culture solution containing bovine serum.

1.1 Cells Isolated from Fat Tissues

In the present invention, any fat tissues obtained from mammalians can be used without particular limitation. Specifically, fat tissues obtained from any sites of mammalian embryos, newborns, or adults can be used. Cells can be isolated as individual cells by, for example, accurately isolating and collecting fat tissues under a stereoscopic microscope and subjecting the collected cells to mechanical treatment and/or enzyme treatment such as collagenase or dispase treatment.

The cells isolated from fat tissues in such a manner include fat cells, fat precursor cells, and somatic stem cells. The fat tissue-derived cells that are used in the present invention may comprise such cells. These cells are confirmed to be Lin-negative, c-Kit-negative to weak-positive, and β1 integrin-positive cells.

1.2 Culture Conditions

The isolated cells are cultured in culture solutions prepared by adding adequate amounts of bovine serum to culture solutions that are commonly used for culturing mammalian fat cells, such as DMEM culture solutions, MEM culture solutions, α-MEM culture solutions, RPMI culture solutions, or DMEM/F12 culture solutions. The amount of bovine serum to be added is not particularly limited, and such amount is adequately determined in accordance with the origin or type of cells. The amount of bovine serum to be added is preferably 0% to 20%, and more preferably approximately 5% to 10%. Nutridoma (Behringer), human serum, or the like may be used instead of bovine serum.

Two-dimensional culture is conducted using a commercially available culture dish. Conditions, such as temperature or $CO_2$, are adequately determined in accordance with the properties of the cells to be used. Culture is generally conducted in the presence of 4% to 6% $CO_2$ at 33° C. to 37° C., and particularly preferably in 5% $CO_2$ at approximately 37° C. The duration of cell culture is not particularly limited, and culture may be continued while adequately exchanging media until the expression of required myocardial cells is observed. According to the results of an experiment conducted by the present inventors, beating myocardial cells were observed 3 days after the initiation of culture, and proliferation of spherical myocardial precursor cells (myocardial stem cells) was initiated simultaneously therewith.

During the culture, cytokines that accelerate cell differentiation and proliferation may be adequately added to the culture solution. Examples of such cytokines include: members of the EGF family, such as EGF, TGF-α, HB-EGF, FGF, and HGF; members of the TGF-β family, such as TGF-β; members of the IL family, such as LIF; members of the VEGF family, such as VEGF-A; members of the PDGF family, such as PDGF-AB and PDGF-BB; members of the Ephrin family, such as Ephrin B; and the stem cell factor (SCF). LIF, HB-EGF, and DGF are particularly preferable.

The amount of cytokines to be added is adequately determined in accordance with the properties of cytokines or cells to be used. When the cells isolated from mouse fat tissues are used, it is preferable to add approximately 1,000 u/ml to 5,000 ml of LIF, or approximately 100 ng/ml to 1 µg/ml of HB-EGF, although the amount is not limited to such range.

2. Induction of Differentiation of Bone Marrow Cells or Cord Blood-derived Cells into Myocardial Cells The cells isolated from mammalian fat tissues or a culture supernatant thereof are added to bone marrow cells or cord blood-derived cells, and the resultant is cultured in a culture solution containing bovine serum. Thus, such bone marrow cells or cord blood-derived cells can be induced to differentiate into myocardial precursor cells and/or myocardial cells.

2.1 Cells Isolated from Fat Tissues or Culture Supernatant Thereof

In the aforementioned method, cells may be isolated from fat tissues in accordance with the procedure of the section 1 above. A culture supernatant can be obtained by culturing the isolated fat tissue-derived cells under the conditions described in 1 above for an adequate period of time. The culture duration is not particularly limited; however, it is preferable to use the culture supernatant obtained after culturing for at least 1 day.

2.2 Bone Marrow Cells

The bone marrow cells used in the aforementioned method are not particularly limited as long as they are derived from mammalians. Specifically, any bone marrow-derived cells obtained from mammalian embryos, newborns, or adults can be used. Bone marrow cells are preferably bone marrow stroma cells, and particularly preferably mesenchymal stem cells. Alternatively, fractions of hematopoietic stem cells are preferably used. These bone marrow cells are obtained from mammalians in accordance with a conventional technique. Bone marrow cells are preferably primary cells in culture, and cryopreserved bone marrow cells may also be used.

The bone marrow cells and fat tissues are preferably derived from the same species. Specifically, mouse fat tissue-derived cells are preferably used for mouse bone marrow cells, and rat fat tissue-derived cells are preferably used for rat bone marrow cells.

2.3 Cord Blood-derived Cells

The cord blood-derived cells that are used in the aforementioned method are not particularly limited as long as they are derived from mammalians. Mononuclear cells in the cord blood are preferable. Cells are obtained from the cord blood in accordance with a conventional technique. Cord blood-derived cells and fat tissues are preferably derived from the same species, as with the case of the section above.

2.4 Culture Conditions

The cells are cultured in culture solutions prepared by adding adequate amounts of bovine serum to culture solutions that are commonly used for culturing mammalian cells, such as DMEM culture solutions, MEM culture solutions, α-MEM culture solutions, RPMI culture solutions, or DMEM/F12 culture solutions. The amount of bovine serum to be added is not particularly limited, and such amount is adequately determined in accordance with the origin or type of relevant cells. The amount of bovine serum to be added is preferably 0% to 20%, and more preferably approximately 5% to 10%. Nutridoma (Behringer), human serum, or the like may be used instead of bovine serum.

The cells isolated from fat tissues are added to the bone marrow cells or cord blood-derived cells, and the resultant is subjected to two-dimensional culture using a commercially available culture dish. Alternatively, coculture is carried out under conditions where the fluid factor of the cells isolated from fat tissues can intercommunicate with the fluid factor of the bone marrow cells or cord blood-derived cells. The ratio of the bone marrow cells or cord blood-derived cells to be mixed with the cells isolated from fat tissues (the cell count ratio) is preferably 1:1 to 10. The ratio of bone marrow cells to be mixed with the cells isolated from fat tissues is particularly preferably approximately 1:4.

When the culture supernatant of the fat tissue-derived cells is added to the bone marrow cells or cord blood-derived cells, the culture supernatant of the cells that had been cultured for the aforementioned adequate duration, i.e., for at least 1 day, is added to the bone marrow cells or cord blood-derived cells, and the resultant is then subjected to two-dimensional culture. The amount of the culture supernatant to be added is not particularly limited, and such amount is adequately determined in accordance with the type of cells used. In the case of mouse bone marrow cells, fat tissue-derived cells are cultured in amounts of 1 to 10 times and preferably 4 times that of the bone marrow cells, and the resulting culture supernatant is preferably used.

Conditions such as temperature or $CO_2$ are adequately determined in accordance with the properties of the cells to be used. Culture is generally conducted in the presence of 4% to 6% $CO_2$ at 33° C. to 37° C., and particularly preferably in 5% $CO_2$ at approximately 37° C. The culture duration is not particularly limited, and culture may be continued while adequately exchanging media until the expression of required myocardial cells is observed. According to the results of an experiment conducted by the present inventors, beating myocardial cells were observed 7 days after the initiation of culture, and proliferation of spherical myocardial precursor cells (myocardial stem cells) was initiated simultaneously therewith. Further, approximately 20 to 60 colonies deduced to be myocardial cells were generated 1 to 2 weeks after the initiation of culture.

During the culture, cytokines that accelerate cell differentiation and proliferation may be adequately added to the culture solution. Examples of such cytokines include: members of the EGF family, such as EGF, TGF-α, HB-EGF, FGF, and HGF; members of the TGF-β family, such as TGF-β; members of the IL family, such as LIF; members of the VEGF family, such as VEGF-A; members of the PDGF family, such as PDGF-AB and PDGF-BB; members of the Ephrin family, such as Ephrin B; and the stem cell factor (SCF). LIF, HB-EGF, and PDGF are particularly preferable.

The amount of cytokines to be added is adequately determined in accordance with the properties of cytokines or cells to be used. When the cells isolated from mouse fat tissues are used, it is preferable to add approximately 1,000 u/ml to 5,000 ml of LIF, approximately 100 ng/ml to 1 µg/ml of HB-EGF, or approximately 1 ng/ml to 50 ng/ml of PDGF-AB, although the amount is not limited to such range.

3. Myocardial Cells Induced to Differentiate from Fat Tissues, Bone Marrow Cells, or Cord Blood-derived Cells The present invention provides myocardial precursor cells and/or myocardial cells prepared by any of the aforementioned methods. The term "myocardial precursor cells" used herein refers to cells that can be differentiated into myocardial cells, and this term also refers to myocardial stem cells.

These myocardial precursor cells exhibit morphological properties, protein expression, and gene expression peculiar to myocardial cells, unlike their original cells. For example, abundant mitochondria, ANP granules, and Z bands are observed in myocardial cells under an electron microscope. Myocardial cells are observed as spindle-shaped beating cells, they gradually assemble to form a sheet, and they are synchronized to beat under an inverted microscope. Also, the myocardial precursor cells are observed to be rounder than such cells and spherical, they gradually become spindle-shaped, and they begin beating. In the case of protein expression, the expression of sarcomeric actin (α-Sarcomeric Muscular Actin (Sr-1)) and that of cardiac actin that are peculiar to myocardial cells are observed. In the case of gene expression, expression of α,β-MHC, MLC-2v, or BNP that are peculiar to myocardial cells or expression of the expression factors GATA-4 or NKX2.5 is observed. Accordingly, it was confirmed that the differentiated cells were myocardial cells or myocardial precursor cells, based on such characteristics.

4. Applications of Myocardial Cells Differentiated from Fat Tissues, Bone Marrow Cells, or Cord Blood-derived Cells 4.1 Applications in Regenerative Medicine The myocardial cells and myocardial precursor cells obtained from fat tissues, bone marrow cells, or cord blood-derived cells in the present invention are observed to have the traits of general myocardial cells and myocardial precursor cells under an electron microscope. Also, gene or protein expression patterns thereof are consistent with those of general myocardial cells and myocardial precursor cells. Upon transplantation of these myocardial precursor cells or myocardial cells into a rat model of myocardial infarction, they are synchronized with the myocardial cells of the host to function as myocardial cells. If fat tissues, bone marrow cells, or cord blood-derived cells obtained from the mammalians to which such cells are to be transplanted are used, myocardial precursor cells or myocardial cells that can be transplanted into the mammalians without rejection can be obtained. Specifically, the myocardial precursor cells or myocardial cells obtained by the method of the present invention can be suitably used for heart regeneration.

At present, revascularization in the ischemic area, which was generated upon myocardial infarction, is carried out via local transplantation of vascular stem cells obtained from a large amount of bone marrow fluid. Bone marrow fluid is sampled under general anesthesia, which imposes risks on elderly patients. In contrast, fat tissue sampling can be carried out via simple local anesthesia of skin, and a life-threatening risk is rarely imposed on patients. In addition, fat tissue materials are abundant. Accordingly, a technique of heart regeneration according to the present invention contributes remarkably to the medical field.

4.2 Applications in Screening Systems

The myocardial cells and myocardial precursor cells obtained from fat tissues, bone marrow cells, or cord blood-derived cells in the present invention are observed to have the traits of general myocardial cells and myocardial precursor cells under an electron microscope. Also, gene or protein expression patterns thereof are consistent with those of general myocardial cells and myocardial precursor cells. Accordingly, a test substance is added to the myocardial precursor cells and/or myocardial cells, the resultant is cultured, and phenotypic changes (i.e., changes in morphology or protein expression) or genotypic changes (changes in gene expression) are compared with those of the myocardial precursor cells and/or myocardial cells to which the test substance has not been added. Thus, sensitivity of myocardial cells to the test substance or effects of the test substance on myocardial cells can be evaluated. This evaluation system can be applied to a test of drug sensitivity or screening for therapeutic agents for heart diseases.

EXAMPLES

Example 1

Differentiation of Fat Tissues into Myocardial Cells

Fat tissues (about 1.5 ml) were removed from the cervical or abdominal region of a mouse or rat, the tissues were sliced using ophthalmic surgery scissors, and the sliced tissues were immersed in 1 ml of dispase solution at 37° C. for 15 minutes to loosen the cells. The cells were then filtered through a 40-micron nylon mesh filter, sowed at a cell density of $1\times10^6$ cells/ml, and then subjected to two-dimensional culture on a 24-well culture dish (diameter: about 1.3 cm) in 5% $CO_2$ at 37° C. using a DMEM medium containing 10% FCS.

FIG. 1 shows the results of culturing mouse fat cells. Beating myocardial cell-like cells were observed 3 days after the initiation of culture, and proliferation of spherical myocardial precursor/stem cell-like cells was initiated simultaneously therewith. Myocardial cells can be identified by abundant mitochondria, ANP granules, and Z bands with the use of a stereoscopic microscope, and by morphological traits such as beating and spindle shapes with the use of an inverted microscope. Spindle-shaped cells appeared approximately 1 week after the initiation of culture, and a sheet structure was observed 2 or 3 weeks after the initiation of culture. Colonies (approximately 200 to 300) of myocardial cells were observed in each well 1 week after the initiation of culture.

Example 2

Immunostaining

In order to confirm that the cells obtained in Example 1 had the characteristics of myocardial cells, immunostaining was carried out using a fluorescence-labeled anti-sarcomeric actin (α-Sarcomeric muscular Actin (Sr-1)) antibody (Dako) or anti-cardiac actin (MBL). Sarcomeric actin and cardiac actin are proteins that exhibit expression patterns peculiar to myocardial cells.

Figure 2:
FIG. 2 shows the results of immunostaining fat tissues 14 days after the initiation of culture (A: anti-sarcomeric actin (SA) antibody; B: anti-cardiac actin antibody).
Figure 2:
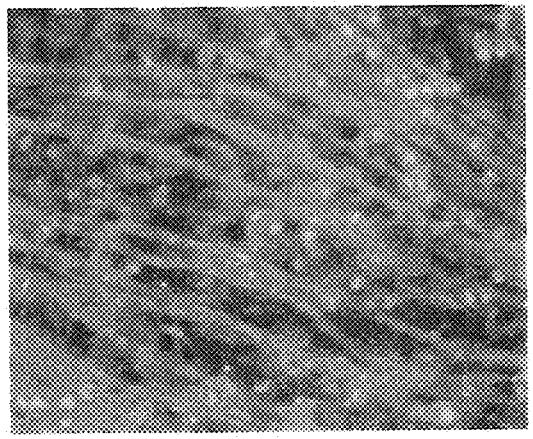

Immunostaining was carried out by culturing mouse fat tissue-derived cells in the same manner as in Example 1 for 14 days and then adding 1 μg/ml of antibody thereto. The results are shown in FIG. 2. As is apparent from FIG. 2, the cultured cells were labeled by the green-fluorescence, which indicates that they were sarcomeric actin- and cardiac actin-positive cells.

Figure 3:
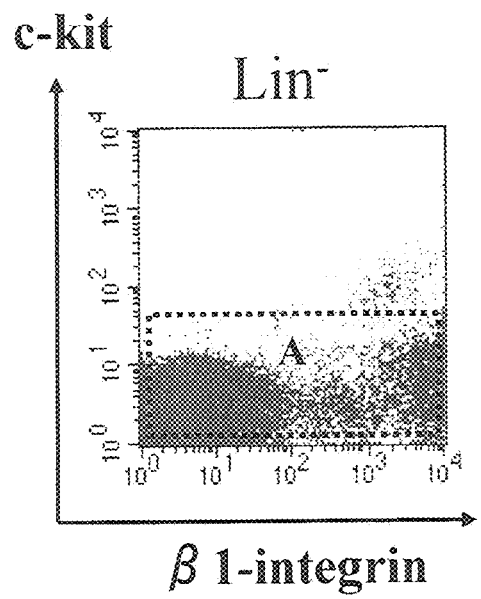
FIG. 3 shows the results of fractionation via flow cytometry (left) and the results of culturing the fractionated Lin-negative β1 integrin-positive cells in vitro and immunostaining the resultant with an anti-SA antibody (right).
Figure 3:
Figure 3:
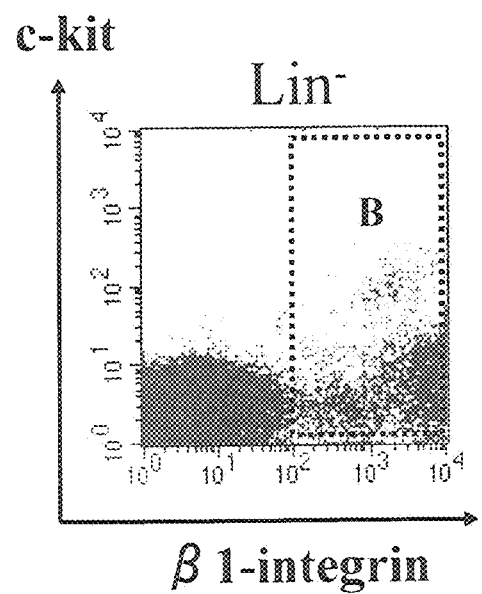
Figure 3:
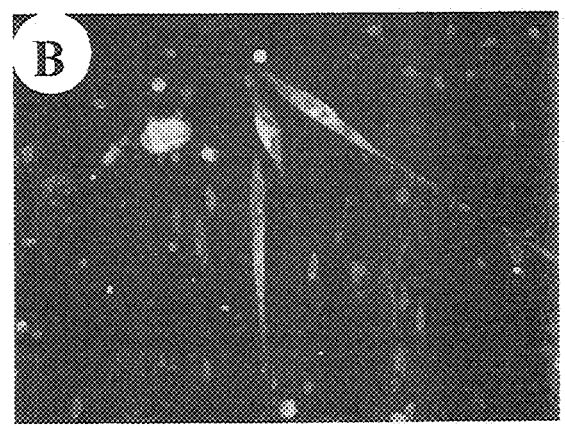

The fat tissues were allowed to disperse in the same manner as in Example 1, staining was carried out using the Lin antibody (a mixture of CD4, CD8, Gr-1, Mac-1, and TER119 (Pharmingen) that can recognize mature blood cells), c-Kit antibody (Pharmingen), or β1 integrin antibody (Pharmingen), and the cells were fractionated using an autofluorescence-activated cell sorter (Epics Altra, Coulter) via flow cytometry. The obtained cells ($10^4$ cells each) were mixed with a DMEM culture solution containing 10% bovine serum, and the mixture was cultured on a 24-well culture dish in the same manner as in Example 1. As a result, sarcomeric actin-positive myocardial cells, which were the same as those obtained in Example 1, were found to be efficiently developed from Lin-negative, c-Kit-negative to weak positive cells, or Lin-negative β1 integrin-positive cells (the cell mass shown in FIG. 3) (FIG. 3).

Example 3

Gene Expression Analysis

In order to confirm that the cells obtained in Example 1 are myocardial cells, gene expression analysis was carried out via RT-PCR. At the outset, mouse fat tissue-derived cells were cultured in the same manner as in Example 1 for 14 days, total RNA was extracted using the RNeasy Mini Kit (Qiagen), and the extracted total RNA was reversely transcribed into cDNA using the PCR kit (Clontech). Subsequently, RT-PCR was carried out with the Advantage polymerase Mix (Clontech) and using the following PCR primers for detecting α,β-MHC, α-skeletal A, α-cardiac A, MLC-2a,2v, and BNP.

```
α-MHC-S
                                      (SEQ ID NO: 1)
5'-tgt ctg ctc tcc acc ggg aaa atc t-3'

α-MHC-AS
                                      (SEQ ID NO: 2)
5'-cat ggc caa ttc ttg act ccc atg a-3'

β-MHC-S
                                      (SEQ ID NO: 3)
5'-aac cca ccc aag ttc gac aag atc g-3'

β-MHC-AS
                                      (SEQ ID NO: 4)
5'-cca act ttc ctg ttg ccc caa aat g-3'

α-skeletal A-S
                                      (SEQ ID NO: 5)
5'-gga gat tgt gcg cga cat caa aga g-3'

α-skeletal A-AS
                                      (SEQ ID NO: 6)
5'-tgg tga tcc aca tct gct gga agg t-3'

α-cardiac A-S
                                      (SEQ ID NO: 7)
5'-gac cac cgc ttt ggt gtg tga caa t-3'

α-cardiac A-AS
                                      (SEQ ID NO: 8)
5'-gcc aga atc cag aac aat gcc tgt g-3'

MLC-2a-S
                                      (SEQ ID NO: 9)
5'-agc agg cac aac gtg gct ctt cta a-3'

MLC-2a-AS
                                      (SEQ ID NO: 10)
5'-cct ggg tca tga gaa gct gct tga a-3'

MLC-2v-S
                                      (SEQ ID NO: 11)
5'-atg gca cct ttg ttt gcc aag aag c-3'

MLC-2v-AS
                                      (SEQ ID NO: 12)
5'-ccc tcg gga tca aac acc ttg aat g-3'

BNP-S
                                      (SEQ ID NO: 13)
5'-aaa agt cgg agg aaa tgg ccc aga g-3'

BNP-AS
                                      (SEQ ID NO: 14)
5'-tgc ctg agg gga aat gct cag aac t-3'

(S: sense primer; AS: anti-sense primer)
```

Figure 4:
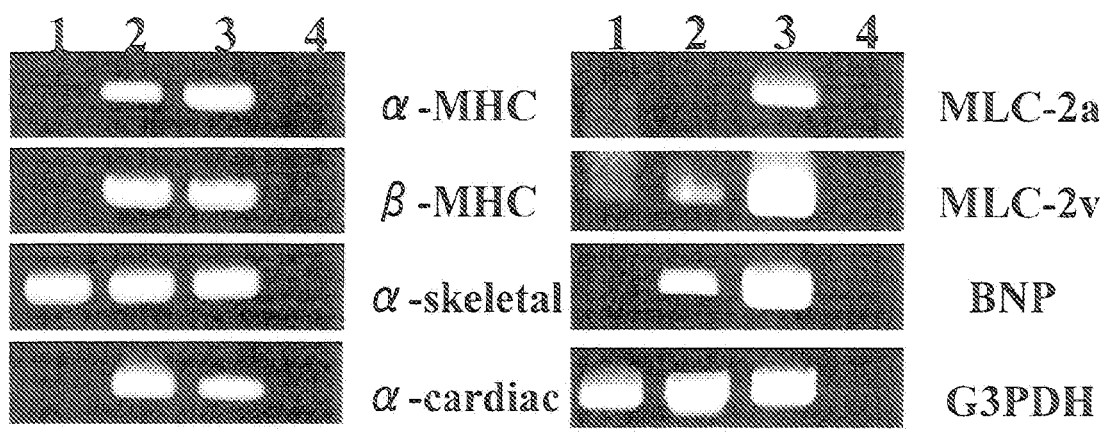
FIG. 4 shows the results of gene expression analysis (RT-PCR) in cells differentiated from fat tissues.

The results are shown in FIG. 4. In each line of FIG. 4, "1" represents fat tissues immediately after sampling; "2" represents cultured cells; "3" represents myocardial cells derived from a mouse heart; and "4" represents water. As is apparent from FIG. 4, expression of α,β-MHC, α-skeletal A, α-cardiac A, MLC-2v, and BNP specific to myocardial cells was observed in the cultured cells.

Example 4

Analysis of Nuclear Transcription Factor

The expressions of the nuclear transcription factors, i.e., the GATA-4 and NKX2.5 genes, specific to myocardial cells were analyzed. Analysis was carried out by obtaining cDNA in accordance with the method described in Example 3 and conducting RT-PCR using the following PCR primers for detecting GATA-4 and NKX2.5.

```
Nkx2.5-S
                                      (SEQ ID NO: 15)
5'-tct ggt tcc aga acc gtc gct aca a-3'

Nkx2.5-AS
                                      (SEQ ID NO: 16)
5'-atc gcc ctt ctc cta aag gtg gga gt-3'

GATA4-S
                                      (SEQ ID NO: 17)
5'-gag tgt gtc aat tgt ggg gcc atg t-3'

GATA4-AS
                                      (SEQ ID NO: 18)
5'-tgc tgc tag tgg cat tgc tgg agt t-3'

(S: sense primer; AS: anti-sense primer)
```

Figure 5:
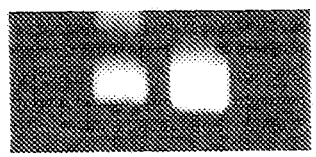
FIG. 5 shows the results of analyzing the nuclear transcription gene (RT-PCR) in cells differentiated from fat tissues.
Figure 5:
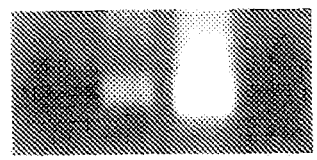
Figure 5:
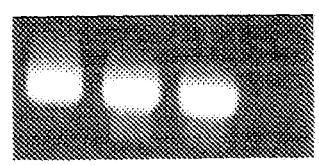

The results are shown in FIG. 5. In each line of FIG. 5, "1" represents fat tissues immediately after sampling; "2" represents cultured cells; "3" represents myocardial cells derived from a mouse heart; and "4" represents water. As is apparent from FIG. 5, expressions of the myocardial cell-specific transcription factors, i.e., the GATA-4 and NKX2.5 genes, were observed in the cultured cells.

Example 5

Optimization of Culture Conditions (Differentiation of Fat Tissues into Myocardial Cells)

2,000 U/ml of leukemia inhibitory factor (LIF), 0.5 μg/ml of HB-EGF, and 2,000 U/ml of LIF in combination with 0.5 μg/ml of HB-EGF were independently added to DMEM culture solutions each containing 10% FCS, and the resultants were cultured in the same manner as in Example 1. The cultured cells were subjected to immunostaining with the α-sarcomeric actin and cardiac actin antibodies in the same manner as in Example 2. Based on the resulting fluorescence intensities, the number of expressed myocardial cells was compared with that resulting when no addition took place using a fluorescence microscope (1×70, Olympus) (4 samples each).

As a result, differentiation into myocardial cells was found to be accelerated with the addition of LIF alone, although there was no significant difference from the cells to which no LIF had been added. When HB-EGF was added alone, a significant difference of $p<0.05$ was observed in comparison with the case where HB-EGF was not added, which indicates that differentiation into myocardial cells was accelerated. With the addition of LIF and HB-EGF, a significant difference of $p<0.05$ was observed, which indicates that the differentiation into myocardial cells was accelerated to the greatest extent.

Example 6

Experiment Involving Transplantation into Rat Model of Myocardial Infarction Rat models of myocardial infarction were prepared by subjecting male SD rats (N=19) to artery ligature to induce myocardial infarction. Rat fat tissue-derived cells were isolated in accordance with the procedure of Example 1, and the isolated cells were cultured in a DMEM culture solution containing 10% FCS to obtain fat tissue-derived myocardial cells. The resulting fat tissue-derived myocardial cells were injected into the locations of myocardial infarction (0.1 ml each of cells at a concentration of $2 \times 10^6$ cells/ml to 5 locations) of the rat models of myocardial infarction (N=9), and such rat models were designated as a test group. As a comparison group and a control group, rat models of myocardial infarction to which PBS had been administered (N=10) and noninfarcted sham-operated rats (N=6) were prepared. These groups were analyzed for improvement in heart functions 28 days after injection via ultrasonic diagnosis of the heart. As a result, the comparison group to which PBS had been injected was found to exhibit deterioration in heart functions to a level that was approximately 1/5 the level of the heart functions of normal rats. In contrast, the test group to which fat tissue-derived myocardial cells had been injected exhibited deterioration in heart functions as minor as deterioration to a level that was about 4/5 the level of the heat functions of the normal rats.

Example 7

Coculture of Fat Tissue-Derived Cells and Bone Marrow-derived Cells

The cells derived from mouse fat tissues isolated in accordance with the procedure of Example 1 ($1 \times 10^6$ cells) were mixed with the bone marrow cells ($1 \times 10^5$ cells/ml) labeled with the PKH67 Green Fluorescent Cell Linker Kit (Sigma), the resultant was mixed with 1 ml of DMEM culture solution containing 10% FCS, and the mixture was cultured on a 24-well culture dish (diameter: about 1.3 cm). As a comparison, the bone marrow cells labeled with fluorescent PKH67 were cultured alone under the same conditions.

Figure 6:
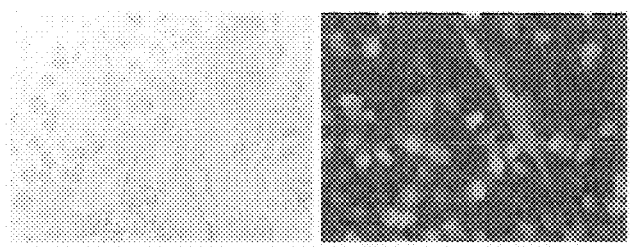
FIG. 6 shows the results of culturing fat tissue-derived cells with bone marrow cells (A: the results of culturing of fat tissue-derived cells with bone marrow cells; B: the results of culturing of bone marrow cells alone).
Figure 6:
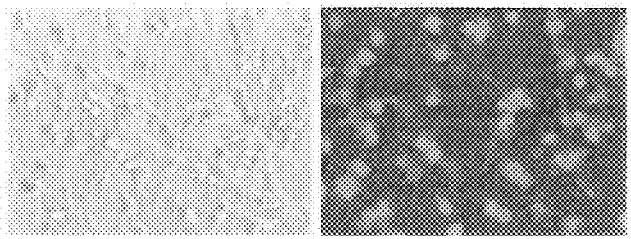

The results are shown in FIG. 6. The bone marrow cells that had been cultured together with fat tissue-derived cells generated about 20 to 60 colonies that were deduced to be myocardial cells 1 or 2 weeks after the initiation of culture. Such myocardial cell colonies included cells derived from bone marrow that had been labeled with fluorescent PKH67 (FIG. 6A). In contrast, differentiation into myocardial cells was not observed in the bone marrow cells that had been cultured alone (FIG. 6B).

Example 8

Optimization of Culture Conditions

Figure 7:
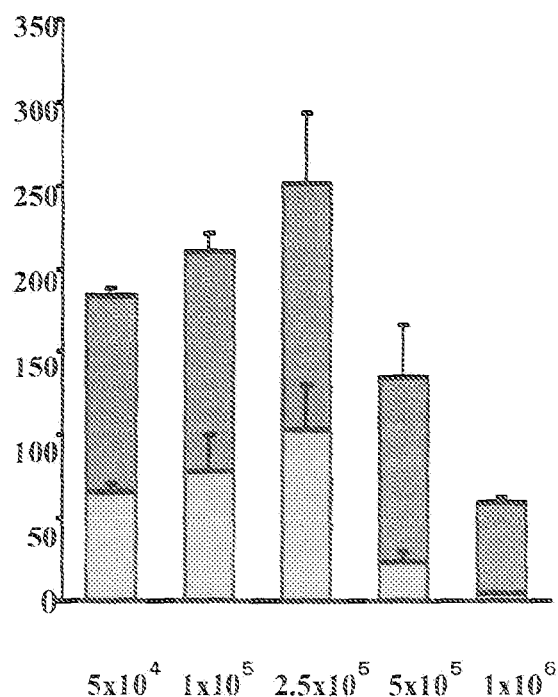
FIG. 7 is a chart showing the changes in the colony count of myocardial cells (vertical axis: colonies/well) obtained when a bone marrow cell count is changed in relation to a fat tissue-derived cell count (horizontal axis: cells). In this chart, the top of each bar chart represents the resulting colony count of the myocardial cells obtained from bone marrow-derived cells and the bottom of each chart represents the colony count of the myocardial cells obtained from myocardial tissues.

Fat tissue-derived cells ($1 \times 10^6$ cells) were subjected to culture together with $5 \times 10^4$, $1 \times 10^5$, $2.5 \times 10^5$, $5 \times 10^5$, or $1 \times 10^6$ bone marrow-derived cells to examine the influences thereof. The results are shown in FIG. 7. As is apparent from FIG. 7, when mixing with $2.5 \times 10^5$ bone marrow cells took place, i.e., when fat tissues were cultured with bone marrow cells in an amount equal to one-fourth of the amount of fat tissue-derived cells, the number of resulting myocardial cells derived from the fluorescent PKH67-labeled bone marrow cells was found to be maximal.

Example 9

Factors that Affect Differentiation of Bone Marrow Cells

In order to examine factors that affect differentiation of bone marrow cells, fat tissue-derived cells and bone marrow cells were cultured in the same manner as in Example 8, except that they were separated from each other with a membrane having 0.4-micron pores (Cell culture insert, Falcon). As a result, adhesion between adjacent cells was inhibited, and differentiation of bone marrow cells into myocardial cells was observed under the conditions where only the fluid components intercommunicated with each other. This indicates that a culture supernatant obtained from a system that induces fat tissues to differentiate into myocardial cells contains fluid molecules that induce bone marrow cells to differentiate into myocardial cells.

Example 10

Differentiation of Human Fat Tissues into Myocardial Cells

Cells were isolated from fat tissues in the aortic region and omental area of the human heart, and the isolated cells were immersed in 5 ml of dispase solution at 37° C. for 30 minutes to loosen the cells. The cells were then filtered through a 40-micron nylon mesh filter, sowed at a cell density of $1 \times 10^6$ cells/ml on a DMEM medium containing 10% FCS, and then subjected to two-dimensional culture on a 24-well culture dish (diameter: about 1.3 cm) in 5% $CO_2$ at 37° C.

The cells 2 weeks after the initiation of culture were subjected to immunostaining with the anti-sarcomeric actin (SA) antibody. As a negative control, the cells were subjected to staining in the same manner as with a secondary antibody, i.e., with an anti-mouse immunoglobulin. As a result, differentiation of human fat tissues into SA-positive myocardial cells was observed (FIG. 8 (A), upper column).

Figure 8:
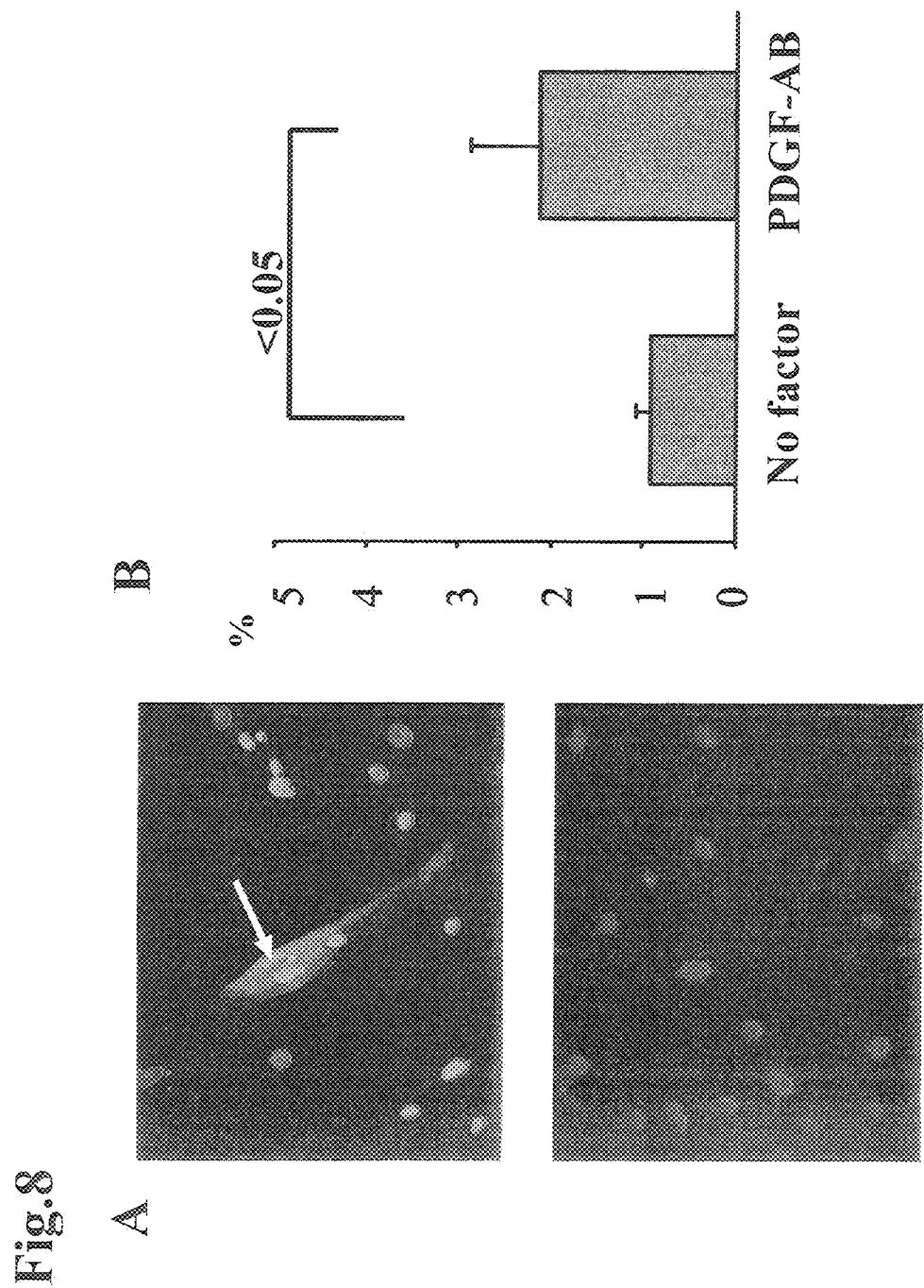
FIG. 8 shows the results of inducing human fat tissues to differentiate into myocardial cells, wherein A represents the results of immunostaining with an anti-SA antibody (upper part: an arrow indicates a myocardial cell; lower part: a negative control) and B represents the percentage of SA-positive cells in relation to the total number of adhesive cells (right: with the addition of PDGF-AB; left: without the addition of PDGF-AB).

Further, 10 ng/ml of PDGF-AB (Invitrogen) was added so as to conduct culturing in the same manner for 2 weeks, the number of SA-positive cells in relation to the total number of adhered cells was determined randomly in 5 fields under a fluorescent microscope (×20), and the result was compared with the number resulting when no PDGF-AB had been added (FIG. 8 (C)). As a result, approximately 1% of the total adhered cells were found to be SA-positive when PDGF-AB was not added. On the contrary, the number of SA-positive myocardial cells was approximately 2 times higher when PDGF-AB was added.

Example 11

Figure 9:
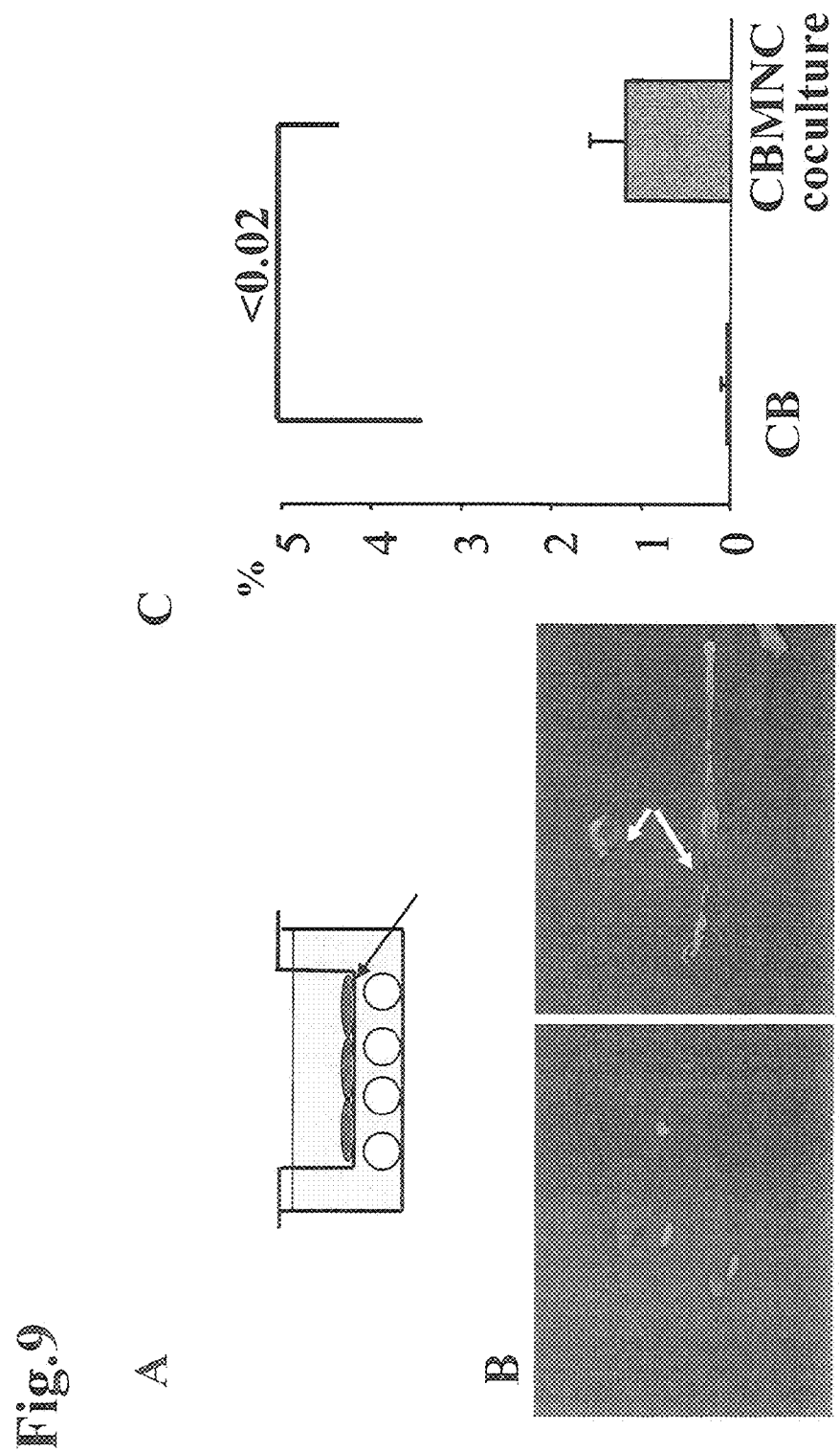
FIG. 9 shows the results of inducing human cord blood mononuclear cells (hCBMNC) to differentiate into myocardial cells, wherein A represents a method of coculture involving separation of hCBMNC (lower part) from mouse fat tissues (upper part) with a cell culture insert (indicated by an arrow), B represents the results of immunostaining with an anti-SA antibody (right: coculture; left: culture of hCBMNC alone), and C represents the percentage of SA-positive cells in relation to the total number of adhesive cells (right: coculture; left: culture of hCBMNC alone).

Differentiation of Cord Blood-derived Cells into Myocardial Cells via Culture of Mouse Fat Tissues and Human Cord Blood A fraction of mononuclear cells was isolated from the human cord blood (CB) with the use of the Ficoll-Paque Plus. In accordance with the procedure of Example 1, cells were separated from mouse fat tissues. As shown in FIG. 9 (A), $1 \times 10^6$ cells/ml of human cord blood mononuclear cells (hCB-MNC) were separated from $2 \times 10^5$ cells/ml of mouse fat tissue-derived cells (BATDC) with a membrane having 0.4-micron pores (Cell culture insert, Falcon), and they were subjected to separate culture. The cells were subjected to two-dimensional culture using a DMEM medium containing 10% FCS in 5% $CO_2$ at 37° C. As a control, $1\times10^6$ cells/ml of hCBMNC were cultured alone under the same conditions on a 24-well culture dish.

The cells 2 weeks after the initiation of culture were subjected to immunostaining with the anti-sarcomeric actin (SA) antibody. As a result, differentiation of hCBMNC into SA-positive myocardial cells was observed (FIG. 9 (B), right column). When hCBMNC was cultured alone, however, differentiation into myocardial cells was not observed (FIG. 9 (B), left column). Further, the number of SA-positive cells in relation to the total number of adhered cells was determined randomly in 5 fields under a fluorescent microscope (×20). When hCBMNC was cultured with BATDC, approximately 1% of the total adhered cells were found to be SA-positive myocardial cells.

All publications, patents, and patent applications cited herein are incorporated herein by reference in their entirety.

INDUSTRIAL APPLICABILITY

The myocardial cells and myocardial precursor cells obtained in present invention are equivalent to general myocardial cells in terms of both phenotypes and genotypes. Accordingly, these cells can be suitably applied to regenerative medicine for the heart region. These cells can also be applied to the evaluation of drug sensitivity of myocardial cells or screening for therapeutic agents for heart diseases.

Sequence Listing Free Text

SEQ ID NO: 1—description of artificial sequence: primer (α-MHC-S)
SEQ ID NO: 2—description of artificial sequence: primer (α-MHC-AS)
SEQ ID NO: 3—description of artificial sequence: primer (β-MHC-S)
SEQ ID NO: 4—description of artificial sequence: primer (β-MHC-AS)
SEQ ID NO: 5—description of artificial sequence: primer (α-skeletal A-S)
SEQ ID NO: 6—description of artificial sequence: primer (α-skeletal A-AS)
SEQ ID NO: 7—description of artificial sequence: primer (α-cardiac A-S)
SEQ ID NO: 8—description of artificial sequence: primer (α-cardiac A-AS)
SEQ ID NO: 9—description of artificial sequence: primer (MLC-2a-S)
SEQ ID NO: 10—description of artificial sequence: primer (MLC-2a-AS)
SEQ ID NO: 11—description of artificial sequence: primer (MLC-2v-S)
SEQ ID NO: 12—description of artificial sequence: primer (MLC-2v-AS)
SEQ ID NO: 13—description of artificial sequence: primer (BNP-S)
SEQ ID NO: 14—description of artificial sequence: primer (BNP-AS)
SEQ ID NO: 15—description of artificial sequence: primer (Nkx2.5-S)
SEQ ID NO: 16—description of artificial sequence: primer (Nkx2.5-AS)
SEQ ID NO: 17—description of artificial sequence: primer (GATA4-S)
SEQ ID NO: 18—description of artificial sequence: primer (GATA4-AS)

What is claimed is:

1. A method for differentiating mammalian bone marrow cells or cord blood-derived cells into myocardial precursor cells and/or myocardial cells without genetic engineering comprising:
   culturing said bone marrow cells or cord blood-derived cells with Lin-negative, c-Kit-negative, and β1 integrin-positive cells isolated from mammalian fat tissues, wherein said bone marrow cells or cord blood-derived cells are induced to differentiate into myocardial precursor cells and/or myocardial cells, and
   wherein the cord blood-derived cells are mononuclear cells, that can be induced to differentiate into myocardial precursor cells and/or myocardial cells, and wherein the mammalian bone marrow cells are mesenchymal stem cells or hematopoietic stem cells.

2. The method according to claim 1, wherein culture is conducted for at least 1 day using a culture solution containing serum or any substitute thereof.

3. The method according to claim 2, wherein culture is conducted with the addition of at least one cytokine to a culture solution.

4. The method according to claim 3, wherein the cytokine is selected from the group consisting of members of the EGF family, members of the TGF-β family, members of the IL family, members of the VEGF family, members of the PDGF family, members of the Ephrin family, and SCF.

5. The method according to claim 1, wherein the bone marrow cells or cord blood-derived cells are mixed with the cells isolated from fat tissues at a ratio of 1:1 to 1:10.

6. The method according to claim 1, wherein the myocardial precursor cells and/or myocardial cells are sarcomeric actin-positive cells.

7. The method according to claim 4, wherein said cytokine is EGF, TGF-α, HB-EGF, FGF or HGF.

8. The method according to claim 4, wherein said cytokine is PDGF-AB or PDGF-BB.

9. The method according to claim 1, wherein said mammalian bone marrow cells or cord blood-derived cells are derived from the same species as said cells isolated from mammalian fat tissues or a culture supernatant thereof.

10. The method according to claim 1, wherein the bone marrow cells or cord blood-derived cells are mixed with the cells isolated from fat tissues at a ratio of 1:4.

* * * * *

```
                        SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (alpha-MHC-S)

<400> SEQUENCE: 1
tgtctgctct ccaccgggaa aatct                                    25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (alpha-MHC-AS)

<400> SEQUENCE: 2
catggccaat tcttgactcc catga                                    25

<210> SEQ ID NO 3
<211> LENGTH: 25
<212> TYPE: DNA
<213> ORGANISM: Artificial Sequence
```

```
<220> FEATURE:
<223> OTHER INFORMATION: Description of Artificial Sequence:
      Synthetic primer (beta-MHC-S)

<400> SEQUENCE: 3
aacccaccca agttcgacaa gatcg                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (beta-MHC-AS)

<400> SEQUENCE: 4
ccaactttcc tgttgcccca aaatg                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (alpha-skeletal A-S)

<400> SEQUENCE: 5
ggagattgtg cgcgacatca aagag                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (alpha-skeletal A-AS)

<400> SEQUENCE: 6
tggtgatcca catctgctgg aaggt                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (alpha-cardiac A-S)

<400> SEQUENCE: 7
gaccaccgct ttggtgtgtg acaat                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (alpha-cardiac A-AS)

<400> SEQUENCE: 8
gccagaatcc agaacaatgc ctgtg                                              25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
```

-continued

Synthetic primer (MLC-2a-S)

<400> SEQUENCE: 9
agcaggcaca acgtggctct tctaa                                        25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (MLC-2a-AS)

<400> SEQUENCE: 10
cctgggtcat gagaagctgc ttgaa                                        25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (MLC-2v-S)

<400> SEQUENCE: 11
atggcacctt tgtttgccaa gaagc                                        25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (MLC-2v-AS)

<400> SEQUENCE: 12
ccctcgggat caaacacctt gaatg                                        25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (BNP-S)

<400> SEQUENCE: 13
aaaagtcgga ggaaatggcc cagag                                        25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (BNP-AS)

<400> SEQUENCE: 14
tgcctgaggg gaaatgctca gaact                                        25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (Nkx2.5-S)

```
<400> SEQUENCE: 15
tctggttcca gaaccgtcgc tacaa                                         25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:
      Synthetic primer (Nkx2.5-AS)

<400> SEQUENCE: 16
atcgcccttc tcctaaaggt gggagt                                        26

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (GATA4-S)

<400> SEQUENCE: 17
gagtgtgtca attgtggggc catgt                                         25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:
      Synthetic primer (GATA4-AS)

<400> SEQUENCE: 18
tgctgctagt ggcattgctg gagtt                                         25
```